United States Patent
Christian et al.

(10) Patent No.: US 8,542,353 B2
(45) Date of Patent: Sep. 24, 2013

(54) REFRACTIVE INDEX SENSOR FOR FLUID ANALYSIS

(75) Inventors: Sean M. Christian, Land O Lakes, FL (US); Jess V. Ford, Weatherford, TX (US); Bryan Statt, Marion, NY (US); Thomas Blankinship, Fort Worth, TX (US); Dennis Roessler, Fort Worth, TX (US); Christopher Cotton, Honeoye Falls, NY (US); Bryan W. Kasperski, Carrollton, TX (US); Margaret C. Waid, Aledo, TX (US)

(73) Assignee: Precision Energy Services, Inc., Fort Worth, TX (US)

( * ) Notice: Subject to any disclaimer, the term of this patent is extended or adjusted under 35 U.S.C. 154(b) by 232 days.

(21) Appl. No.: 12/894,324

(22) Filed: Sep. 30, 2010

(65) Prior Publication Data

US 2012/0081698 A1     Apr. 5, 2012

(51) Int. Cl.
*G01N 21/41* (2006.01)
*G01N 21/55* (2006.01)

(52) U.S. Cl.
USPC .......................................... 356/128; 356/445

(58) Field of Classification Search
USPC .............. 356/128–137, 445; 250/269.1, 262
See application file for complete search history.

(56) References Cited

U.S. PATENT DOCUMENTS

| | | | |
|---|---|---|---|
| 2,807,976 A | 10/1957 | Vossberg | |
| 3,628,867 A | 12/1971 | Brady | |
| 3,645,631 A * | 2/1972 | Gupta | 356/136 |
| 3,751,672 A * | 8/1973 | Michel et al. | 250/552 |
| 3,999,857 A | 12/1976 | David et al. | |
| 4,264,205 A | 4/1981 | Landa | |
| 4,285,596 A | 8/1981 | Landa | |
| 4,306,805 A * | 12/1981 | Arrington | 356/133 |

(Continued)

FOREIGN PATENT DOCUMENTS

| | | |
|---|---|---|
| EP | 0341927 | 11/1989 |
| EP | 0341927 A1 | 11/1989 |

(Continued)

OTHER PUBLICATIONS

Co-pending U.S. Appl. No. 12/613,808, entitled "Multi-Channel Detector Assmebly for Downhole Spectroscopy," filed Nov. 6, 2009.

(Continued)

*Primary Examiner* — Sang Nguyen
(74) *Attorney, Agent, or Firm* — Wong, Cabello, Lutsch, Rutherford & Brucculeri, LLP

(57) ABSTRACT

A refractive index sensor having one or more sources, an adaptive optical element or scanner, imaging optics, a sensing optic, and one or more detectors. The scanner impinges a signal from the source into the sensing optic and onto a sensor-sample interface at sequential angles of incidence. The detector response increases dramatically to signals reflected from the interface at corresponding sequential angles of reflection equal to or greater than a critical angle. The refractive index sensor also uses an input lens between the scanner and the sensing optic and uses an output lens between the sensing optic and the detector. A processor controls the sensor and can determine index of refraction of the fluid sample based on the detector response and scan rate. The sensor can be used in several operational environments from a laboratory to a downhole tool, such as a formation tester to determine properties in a borehole environment.

35 Claims, 9 Drawing Sheets

(56) References Cited

U.S. PATENT DOCUMENTS

| | | | |
|---|---|---|---|
| 4,487,503 | A * | 12/1984 | Grandjacques et al. ...... 356/136 |
| 4,569,590 | A | 2/1986 | Karney et al. |
| 4,571,082 | A | 2/1986 | Downs |
| 4,632,528 | A | 12/1986 | Yoshino et al. |
| 4,682,889 | A | 7/1987 | Harmer |
| 4,692,024 | A | 9/1987 | Bloss |
| 4,785,806 | A | 11/1988 | Deckelbaum |
| 4,832,490 | A | 5/1989 | Boos |
| 4,834,533 | A | 5/1989 | Horike et al. |
| 4,929,049 | A | 5/1990 | Le Goullon et al. |
| 4,952,055 | A | 8/1990 | Wyatt |
| 4,962,815 | A | 10/1990 | Schultz et al. |
| 4,968,148 | A | 11/1990 | Chow |
| 4,994,671 | A | 2/1991 | Safinya et al. |
| 5,026,139 | A | 6/1991 | Klainer et al. |
| 5,083,018 | A | 1/1992 | Rhyne |
| 5,128,797 | A | 7/1992 | Sachse et al. |
| 5,139,661 | A * | 8/1992 | Kolbert ...... 210/198.2 |
| 5,166,747 | A | 11/1992 | Schroeder et al. |
| 5,167,149 | A | 12/1992 | Mullins et al. |
| 5,170,056 | A | 12/1992 | Berard |
| 5,201,220 | A | 4/1993 | Mullins et al. |
| 5,257,086 | A | 10/1993 | Fateley et al. |
| 5,325,170 | A * | 6/1994 | Bornhop ...... 356/128 |
| 5,337,621 | A | 8/1994 | Spease |
| 5,371,543 | A | 12/1994 | Anderson |
| 5,440,118 | A | 8/1995 | Roscoe |
| 5,504,575 | A | 4/1996 | Stafford |
| 5,563,707 | A * | 10/1996 | Prass et al. ...... 356/517 |
| 5,565,978 | A | 10/1996 | Okubo et al. |
| 5,617,201 | A | 4/1997 | Kahre |
| 5,629,125 | A | 5/1997 | Leblans et al. |
| 5,633,708 | A | 5/1997 | Svendsen |
| 5,663,790 | A | 9/1997 | Ekstrom et al. |
| 5,825,478 | A | 10/1998 | Wilcox |
| 5,828,066 | A | 10/1998 | Messerschmidt |
| 5,859,430 | A | 1/1999 | Mullins et al. |
| 5,939,717 | A | 8/1999 | Mullins |
| 6,055,060 | A * | 4/2000 | Bolduan et al. ...... 356/433 |
| 6,075,595 | A | 6/2000 | Malinen |
| 6,128,078 | A | 10/2000 | Fateley |
| 6,130,439 | A | 10/2000 | Le Menn |
| 6,172,746 | B1 | 1/2001 | Byrne et al. |
| 6,274,865 | B1 | 8/2001 | Schroer et al. |
| 6,301,959 | B1 | 10/2001 | Hrametz et al. |
| 6,350,986 | B1 | 2/2002 | Mullins et al. |
| 6,356,675 | B1 | 3/2002 | Weiss |
| 6,388,251 | B1 | 5/2002 | Papanyan |
| 6,420,695 | B1 | 7/2002 | Grasdepot |
| 6,429,936 | B1 | 8/2002 | Scaduto |
| 6,437,326 | B1 | 8/2002 | Yamate et al. |
| 6,465,775 | B2 | 10/2002 | Mullins et al. |
| 6,474,152 | B1 | 11/2002 | Mullins et al. |
| 6,476,384 | B1 | 11/2002 | Mullins et al. |
| 6,504,943 | B1 | 1/2003 | Sweatt et al. |
| 6,559,945 | B1 | 5/2003 | Grasdepot |
| 6,571,118 | B1 | 5/2003 | Utzinger et al. |
| 6,600,591 | B2 | 7/2003 | Anderson et al. |
| 6,628,376 | B1 * | 9/2003 | Nikitin et al. ...... 356/38 |
| 6,678,050 | B2 | 1/2004 | Pope et al. |
| 6,683,681 | B2 | 1/2004 | DiFoggio et al. |
| 6,693,701 | B2 | 2/2004 | Hansen |
| 6,753,960 | B1 | 6/2004 | Polynkin et al. |
| 6,758,090 | B2 | 7/2004 | Bostrom et al. |
| 6,768,105 | B2 | 7/2004 | Mullins et al. |
| 6,781,691 | B2 | 8/2004 | MacKinnon et al. |
| 6,798,518 | B2 | 9/2004 | DiFoggio et al. |
| 6,870,619 | B1 | 3/2005 | Tenhunen et al. |
| 6,939,717 | B2 | 9/2005 | Jiang |
| 6,967,714 | B2 | 11/2005 | Koops et al. |
| 6,995,360 | B2 | 2/2006 | Jones et al. |
| 6,997,055 | B2 | 2/2006 | DiFoggio |
| 7,002,142 | B2 | 2/2006 | Mullins et al. |
| 7,013,723 | B2 | 3/2006 | Ramakrishnan et al. |
| 7,016,026 | B2 | 3/2006 | DiFoggio et al. |
| 7,024,060 | B2 | 4/2006 | Cardenas-Valencia et al. |
| 7,028,773 | B2 | 4/2006 | Fujisawa et al. |
| 7,075,063 | B2 | 7/2006 | Dong et al. |
| 7,084,392 | B2 | 8/2006 | DiFoggio et al. |
| 7,095,012 | B2 | 8/2006 | Fujisawa et al. |
| 7,173,239 | B2 | 2/2007 | DiFoggio |
| 7,199,871 | B2 | 4/2007 | Frot |
| 7,214,933 | B2 | 5/2007 | DiFoggio et al. |
| 7,262,866 | B2 | 8/2007 | Ivarsson |
| 7,265,830 | B2 | 9/2007 | Wang |
| 7,279,678 | B2 | 10/2007 | Andrews et al. |
| 7,280,214 | B2 | 10/2007 | DiFoggio et al. |
| 7,299,136 | B2 | 11/2007 | DiFoggio et al. |
| 7,321,428 | B2 | 1/2008 | Hunt |
| 7,336,356 | B2 | 2/2008 | Vannuffelen et al. |
| 7,360,924 | B2 | 4/2008 | Henson et al. |
| 7,362,422 | B2 | 4/2008 | DiFoggio et al. |
| 7,375,813 | B2 * | 5/2008 | Wolf et al. ...... 356/433 |
| 7,379,180 | B2 | 5/2008 | Vannuffelen et al. |
| 7,392,697 | B2 | 7/2008 | Chikenji et al. |
| 7,403,680 | B2 | 7/2008 | Simbal |
| 7,440,098 | B2 | 10/2008 | Christian et al. |
| 7,445,043 | B2 | 11/2008 | Mullins et al. |
| 7,456,942 | B1 * | 11/2008 | Curley et al. ...... 356/136 |
| 7,461,547 | B2 | 12/2008 | Terabayashi et al. |
| 7,475,593 | B2 | 1/2009 | Odom |
| 7,508,506 | B2 | 3/2009 | Christian et al. |
| 7,511,813 | B2 | 3/2009 | Vannuffelen et al. |
| 7,526,953 | B2 | 5/2009 | Goodwin et al. |
| 7,609,380 | B2 | 10/2009 | Vannuffelen et al. |
| 7,619,725 | B1 * | 11/2009 | Seaver ...... 356/137 |
| 8,411,262 | B2 | 4/2013 | Ford et al. |
| 2003/0206026 | A1 | 11/2003 | Diakonov et al. |
| 2003/0223068 | A1 | 12/2003 | DiFoggio et al. |
| 2004/0169858 | A1 | 9/2004 | Da Silva |
| 2004/0201850 | A1 | 10/2004 | Hajian et al. |
| 2004/0239923 | A1 | 12/2004 | Adams et al. |
| 2004/0239931 | A1 | 12/2004 | Teichmann et al. |
| 2004/0253735 | A1 | 12/2004 | Vadgama et al. |
| 2005/0185179 | A1 | 8/2005 | Wang |
| 2005/0243312 | A1 | 11/2005 | Geshwind et al. |
| 2005/0262936 | A1 | 12/2005 | DiFoggio |
| 2005/0269499 | A1 | 12/2005 | Jones et al. |
| 2006/0241866 | A1 | 10/2006 | DiFoggio |
| 2006/0243033 | A1 | 11/2006 | Freemark et al. |
| 2007/0013911 | A1 | 1/2007 | DiFoggio |
| 2007/0109537 | A1 | 5/2007 | Vannuffelen |
| 2007/0159625 | A1 | 7/2007 | DiFoggio |
| 2007/0171412 | A1 | 7/2007 | Vannuffelen |
| 2007/0171414 | A1 | 7/2007 | Vannuffelen |
| 2007/0229821 | A1 | 10/2007 | Christian et al. |
| 2007/0238180 | A1 | 10/2007 | DiFoggio et al. |
| 2008/0030739 | A1 | 2/2008 | Hartog et al. |
| 2008/0078544 | A1 | 4/2008 | Christian et al. |
| 2008/0087078 | A1 | 4/2008 | Vannuffelen |
| 2008/0165356 | A1 | 7/2008 | DiFoggio et al. |
| 2008/0173083 | A1 | 7/2008 | Kasperski et al. |
| 2008/0173804 | A1 | 7/2008 | Indo et al. |
| 2008/0173805 | A1 | 7/2008 | Indo et al. |
| 2008/0174777 | A1 | 7/2008 | Carron |
| 2008/0314138 | A1 | 12/2008 | Brady |
| 2009/0059332 | A1 | 3/2009 | DiFoggio et al. |
| 2009/0086211 | A1 * | 4/2009 | Dosaka et al. ...... 356/445 |
| 2009/0166085 | A1 | 7/2009 | Ciglenec et al. |
| 2010/0015612 | A1 | 1/2010 | Pelham et al. |
| 2010/0025112 | A1 | 2/2010 | Sroka et al. |
| 2010/0205139 | A1 | 8/2010 | Xia et al. |

FOREIGN PATENT DOCUMENTS

| | | |
|---|---|---|
| GB | 2391939 A | 2/2004 |
| JP | 61-011636 | 1/1986 |
| WO | 81/00775 | 3/1981 |
| WO | 95/04263 | 2/1995 |

OTHER PUBLICATIONS

Co-pending U.S. Appl. No. 12/613,700, entitled "Multi-Channel Source Assembly for Downhole Spectroscopy," filed Nov. 6, 2009.

Co-pending U.S. Appl. No. 12/613,665, entitled "Filter Wheel Assembly for Downhole Spectroscopy," filed Nov. 6, 2009.

English Abstract of JP 61-011636, obtained from Japanese Patent Office.

Search Report in counterpart European Appl. 11181777.1, dated Sept. 11, 2012.

First Examination Report in counterpart Australian Appl. 2011224006, dated Jul. 13, 2012.

First Office Action in co-pending U.S. Appl. No. 12/894,342, dated Mar. 8, 2012.

Response to First Office Action in co-pending U.S. Appl. No. 12/894,342, filed Sep. 4, 2012.

Cantrell, "The SLIM Spectrometer" Anal. Chem. 2003, 75, pp. 27-35, Department of Chemistry, Oregon State University, 153 Gilbert Hall, Corvallis, Oregon 97331-4001.

Hauser, "A Multi-Wavelength Photometer Based on Light-Emitting Diodes" Talanta, vol. 42, No. 4, pp. 605-612, 1995.

Keranen, "Analytic and Raytrace Modeling of a Miniaturized Infrared Spectrometer Module".

Malinen et al., Sensors and Actuators B 51 (1998) 220-224,"LED-based NIR spectrometer module for hand-held and process analyser applications," dated Jun. 16, 1998.

O'Toole, "Absorbance Based Light Emitting Diode Optical Sensors and Sensing Devices," *Sensors* 2008, 8, pp. 2453-2479; dated Apr. 7, 2008 obtained from www.mdpi.org/sensors.

Palma, "Portable light-emitting diode-based photometer with one-shot optochemical sensors for measurement in the field," dated Oct. 21, 2008, American Institute of Physics.

Schlumberger, "Fundamentals of Formation Testing," ©2006, pp. 1-5, 27-29, 55-67, 99-124, 199-202, Schlumberger Marketing Communications, Sugar Land, Texas, United States.

Schlumberger, "Engineering the Next-Generation Downhole Fluid Analysis Tool," dated May 7, 2007.

OZ Optics, "Silicon Optical Bench Platforms," dated Nov. 14, 2002, obtained from www.ozoptics.com.

Yeh, "A Low Cost LED Based Spectrometer," Journal of the Chinese Chemical Society, 2006, 53, pp. 1067-1072.

Thorlabs Inc., "Stepped Circular Neutral Density Filter," Drawing No. 10661-E01, Part No. NDC-100S-4.

Thorlabs Inc., "Mounted Round Step Variable NDC Filter," Drawing No. 10664-E01, Part No. NDC-100S-4M.

Frentress, "Field Photometer with Nine-Element Filter Wheel," dated Feb. 1964, vol. 3, No. 2, Applied Optics, pp. 303-308.

International Search Report and Written Opinion received in corresponding Application No. PCT/US07/82221, dated May 5, 2008.

International Search Report, International Patent Application No. PCT/US07/080112, mailed on Mar. 25, 2008.

Dudley, Dana, et al., "Emerging Digital Micromirror Device (DMD) Applications," DLP Products New Applications, Texas Instruments, Inc. undated.

Wagner, Eugene P. II, et al., "Construction and Evaluation of a Visible Spectrometer Using Digital Micromirror Spatial Light Modulation," Applied Spectroscopy, vol. 49, No. 11, 1995.

Ford, Joseph E., et al., "Dynamic Spectral Power Equalization Using Micro-Opto-Mechanics," IEEE Photonics Technology Letters, vol. 10, No. 10, Oct. 1998.

Duncan, Walter M., "Dynamic Optical Filtering in DWDM Systems Using the DMD," Solid State Electronics 46 (2002), pp. 1583-1585.

Lerner, J.M., et al., "The Optics of Spectroscopy—A Tutorial," Instruments SA, Inc., 1988.

Spudich, Thomas M., et al., "Potential for using a Digital Micromirror Device as a Signal Multiplexer in Visible Spectrscopy," Applied Spectroscopy, vol. 57, No. 7, 2003.

DeVerse, R. A., et al, "Realization of the Hadamard Multiplex Advantage Using a Programmable Optical Mask in a Dispersive Flat-Field Near-Infrared Spectrometer," Applied Spectroscopy, vol. 54, No. 12, 2000.

Badry, R., et al., "Downhole Optical Analysis of Formation Fluids," Oilfield Review, Jan. 1994.

Schroeder, R., "Slick Engineering," Spie's OE Magazine, May 2003.

Raghuraman, B., "Real-Time Downhold pH Measurement Using Optical Spectroscopy," SPE 93057, Society of Petroleum Engineers, 2005.

Sirkis, J., "Multifunctionality the Key in Challenging Instrumentation Markets," Lightwave Magazine, Mar. 2003.

Meyer, R., "RITMOS: A Micromirror-Based Multi-Object Spectrometer," Proceedings of the SPIE, 2004.

Smits, A.R., "In-Situ Optical Fluid Analysis as an Aid to Wireline Formation Sampling," SPE Formation Evaluation, Jun. 1995.

Texas Instruments, Application Report, "Single Panel DLP Projection System Optics," Mar. 2005.

Texas Instruments, Product Preview, "DMD 0.7 XGA 12.degree. LVDS DMD Discovery," Jul. 2005.

Texas Instruments, Product Preview Data Sheet, "DMD 0.7 XGA 12.degree. DDR DMD Discovery," Aug. 30, 2005.

Texas Instruments, "DMD Discovery 1100 Chip Set," 2004.

Texas Instruments, "DMD Discovery 3000 Digital Controller (DDC3000) Starter Kit Technical Reference Manual," Oct. 2005.

Texas Instruments, "DMD Discovery 1100 Controller Board and Starter Kit," Oct. 2004.

Texas Instruments, "DMD Discovery 1100 Controller Board GUI User's & Programmer's Guide," Sep. 2004, Unavailable.

Baker Hughes, " RCI Reservoir Characterization Instrument," obtained from www.bakerhughesdirect.com, generated on Apr. 8, 2010.

Baker Hughes, "SampleView" 2000, obtained from www.bakerhughesdirect.com, generated on Apr. 19, 2010.

First Examination Report in counterpart Australian Appl. 2011224005, dated Oct. 29, 2012.

First Office Action in counterpart Canadian Appl. 2,752,355, dated Mar. 4, 2013.

First Office Action in counterpart Canadian Appl. 2,752,374, dated Jun. 26, 2013.

* cited by examiner

REFRACTIVE INDEX SENSOR FOR FLUID ANALYSIS

CROSS-REFERENCE TO RELATED APPLICATIONS

This application is filed concurrently with U.S. application Ser. No. 12/894,342, and entitled "Downhole Gas Breakout Sensor," which is incorporated herein by reference in its entirety.

BACKGROUND

Various chemical and physical parameters of a material may be of interest in fluid analysis, process monitoring, and other operations, and a variety of systems can be used to determine such parameters. For example, the index of refraction of a transparent medium may be a parameter of interest in a given operation. A critical angle measurement is one approach that can be used to obtain the index of refraction of an unknown medium.

FIG. 1 helps illustrate index of refraction, critical angle, and other related details. As shown, light rays $R_1$, $R_2$, & $R_3$ pass at different angles through a first transparent medium $M_1$ having a known refractive index $n_1$. The light rays meet the boundary or interface between this first medium $M_1$ and a second medium $M_2$. In this example, the second medium $M_2$ has an unknown index of refraction $n_2$ that is at least less than the known refractive index $n_1$.

A first light ray $R_1$ passing through the first medium $M_1$ at some angle of incidence (i.e., $\theta_i$) toward the interface will have a portion that passes through the interface and refracts in the second medium $M_2$. This first ray $R_1$ will also have another portion that reflects off the interface back into the same medium $M_1$. At one particular angle of incidence called the critical angle $\theta_{crit}$, however, an incident light ray $R_2$ refracts parallel to the interface (i.e., an angle of 90-degrees relative to the normal of the interface) so that the refracted light passes along the boundary between the mediums $M_1$ & $M_2$. Light ray $R_3$ incident at other angles $\theta_{TIR}$ beyond this critical angle $\theta_{crit}$ will be reflected entirely in the first medium $M_1$. This is referred to as Total Internal Reflection (TIR).

The actual value of the critical angle $\theta_{crit}$ depends on the refractive index of the two mediums $M_1$ & $M_2$. Snell's Law can be used to determine the unknown index of refraction of the second medium $M_2$ if the refractive index of $M_1$ is known. Snell's Law is characterized as:

$$\frac{\sin\theta_1}{\sin\theta_2} = \frac{v_1}{v_2} = \frac{n_2}{n_1},$$

where
$\theta_1$ ≡ angle of incidence
$\theta_2$ ≡ angle of refraction
$v_1$ ≡ light velocity in material 1
$v_2$ ≡ light velocity in material 2
$n_1$ ≡ refractive index or material 1
$n_2$ ≡ refractive index of material 2
At the critical angle $\theta_{crit}$ when $n_1 > n_2$ $$\left(\text{i.e.,} \frac{n_2}{n_1} < 1\right),$$

the angle of incidence $\theta_1$ in the equation is the critical angle $\theta_{crit}$, and the angle of refraction $\theta_2$ is 90-degrees relative to the normal of the interface. By measuring the critical angle $\theta_{crit}$ between the mediums $M_1$ & $M_2$ and by already knowing the refractive index $n_1$ of the known medium $M_1$, the unknown refractive index $n_2$ of the second medium $M_2$ can be calculated as: $n_2 = n_1 \sin \theta_{crit}$. Since the refractive index of a medium is dependent on composition, it is possible to estimate the chemical composition of $M_2$.

Devices are known in the art that use a critical angle measurement to measure very specific chemical systems, thin films, and the like. One of the most common devices is the Abbe and Pulfrich refractometer. There are also a number of commercially available critical angle based systems for process monitoring and control. In general, none of the above-mentioned systems or classes of systems are amenable to harsh environments.

There are also other approaches to refractive index measurement, but the operating principals are sufficiently different from the critical angle methodology. As an example, refractive index can be measured by commercially available systems that include Fabry-Perot optical cavities. This type of system is not amenable to harsh environments because of thermal issues with the required electronics and fouling of the measurement region (i.e., the optical cavity) with fluids having viscosities greater than water and/or high particulate loading.

A borehole in a geological formation is an example of a harsh environment where chemical and physical parameters of materials are of interest. Various systems can be conveyed within the borehole during geophysical exploration and production operations to determine the chemical and physical parameters of materials in the borehole environs. These downhole systems can include formation testers and borehole fluid analysis systems that determine parameters of fluids or formation matrix in the vicinity of the borehole as well as materials, such as fluids, within the borehole itself. Preferably, these downhole systems make all measurements in real-time using the available instrumentation in the borehole, although data and fluids can be collected for later retrieval and processing at the surface. In analyzing the fluids, various properties of the fluid may be of interest. For example, the properties include, but are not limited to, fluid density, fluid homogeneity, salinity, gas fraction, asphaltene content, and chemical composition.

One example of such a downhole system is a formation tester tool used in the oil and gas industry to measure pressure, temperature, and other parameters of a formation penetrated by a borehole. (By definition, formation fluid is a complex mixture of liquids and/or gases.) The parametric measurements are typically combined with in-situ or uphole analyses of physical and chemical properties of the formation fluid to evaluate production prospects of reservoirs penetrated by the borehole. When conveyed downhole, the formation tester tool draws fluid into the formation tester tool for pressure measurements, analysis, sampling, and optionally for subsequent exhausting of the fluid into the borehole. Regardless of the fluid sampling methodology, accurate and precise measurements of fluid pressure and temperature are required to obtain meaningful correlations between refractive index and chemical composition.

Some borehole devices are known in the art that can measure index of refraction of a downhole fluid. However, such systems offer only limited dynamic range and resolution of measurement and suffer from other disadvantages. Furthermore, in a non-borehole environment, devices available in the art may also have a limited dynamic measurement range.

SUMMARY

A refractive index sensor determines chemical and physical parameters of mediums or materials. The refractive index sensor disclosed herein utilizes a critical angle approach with a large overall dynamic range and can preferably function across a wide range of environmental conditions.

The refractive index sensor has one or more sources, one or more detectors, sensing optics, an adaptive optical element, and a cooperating processor. A portion of the sensing optic contacts the fluid sample, thereby forming a sensor-sample interface. The adaptive optical element directs signals (i.e., electromagnetic radiation) from one or more sources into the sensing optic. As it directs the signals from the source, the adaptive optical element routes the signals in the time domain and at varying sequential angles into a lens system that further routes the scanned signals into the sensing optic. The sensor's adaptive optical element can be a scanning mirror or refractive optic or can be a multi-sided mirror that oscillates or rotates. Alternatively, the adaptive optical element can be a dynamic diffractive optical element, such as a Liquid Crystal on Silicon (LCoS) element, or a Micro-Optical Electro-Mechanical System (MOEMS) micro-mirror or micro-mirror array.

Depending on the refractive index of the fluid sample at the interface, scanned signals at a plurality of incident angles may reflect from the optic-sample interface. In particular, if the scanned angle of incidence is greater than the critical angle of the optic-sample interface, then the scanned signal reflects from the interface to a detection optical assembly. At this point, a lens system images the reflected signal from the sensing optic onto a detector, which responds to the reflected signal.

As the signal is scanned across the optic-sample interface as a function of time at varying angles of incidence, the detector response is therefore a function of the critical angle at this interface. In turn, the detector response indicative of the critical angle correlates to the unknown refractive index of the fluid sample being analyzed. The processor determines the sample's refractive index from the detector's response and can optionally compute parameters of interest from the determined refractive index. The processor can also use a thermal sensor to determine the temperature of the fluid sample and make environmental corrections in real-time, if needed.

Because the measurements operate in the time domain, apparatus and methods disclosed herein yield a rugged refractive index sensor that is practically insensitive to environmental effects on the source or detector, such as output intensity fluctuations of the source or sensitivity fluctuations of the detector. The sensor is also practically insensitive to background (i.e., dark current) fluctuations in the detector. Sensitivity to intensity fluctuations of the source and dark current variations are typical problems in many existing systems. The disclosed refractive index sensor is also compact and offers a smaller "foot print" when compared to prior art critical angle systems. Compactness is advantageous in all non-laboratory environments where space is at a premium.

In one implementation, the disclosed refractive index sensor disposes in a downhole tool, such as a formation tester tool, for performing fluid analysis in a borehole. The sensor disposed in the downhole tool can determine the index of refraction of a fluid sample from the borehole environs. Additional parameters of interest of the downhole fluid can subsequently be determined from the refractive index measurements.

In other implementations, the disclosed refractive index sensor can be used in variety of host devices, including laboratory instruments, industrial monitors, process monitors, or environmental monitors. For example, a laboratory instrument can use the disclosed refractive index sensor, and the instrument can be a stand-alone device or can be integrated with another process and/or environmental monitor.

The foregoing summary is not intended to summarize each potential embodiment or every aspect of the present disclosure.

BRIEF DESCRIPTION OF THE DRAWINGS

The manner in which the above recited features and advantages, briefly summarized above, are obtained can be understood in detail by reference to the embodiments illustrated in the appended drawings.

DETAILED DESCRIPTION

Details of a refractive index sensor according to the present disclosure are initially discussed along with aspects of its operation. Subsequently, details of the disclosed refractive index sensor described herein are provided for operating in a harsh environment, such as a borehole. Finally, the disclosed refractive index sensor is shown embodied as an element of a formation tester tool (FIG. 9A), a laboratory instrument (FIG. 10A), and an element of a process (FIG. 10B).

A. Refractive Index Sensor

Figure 1:
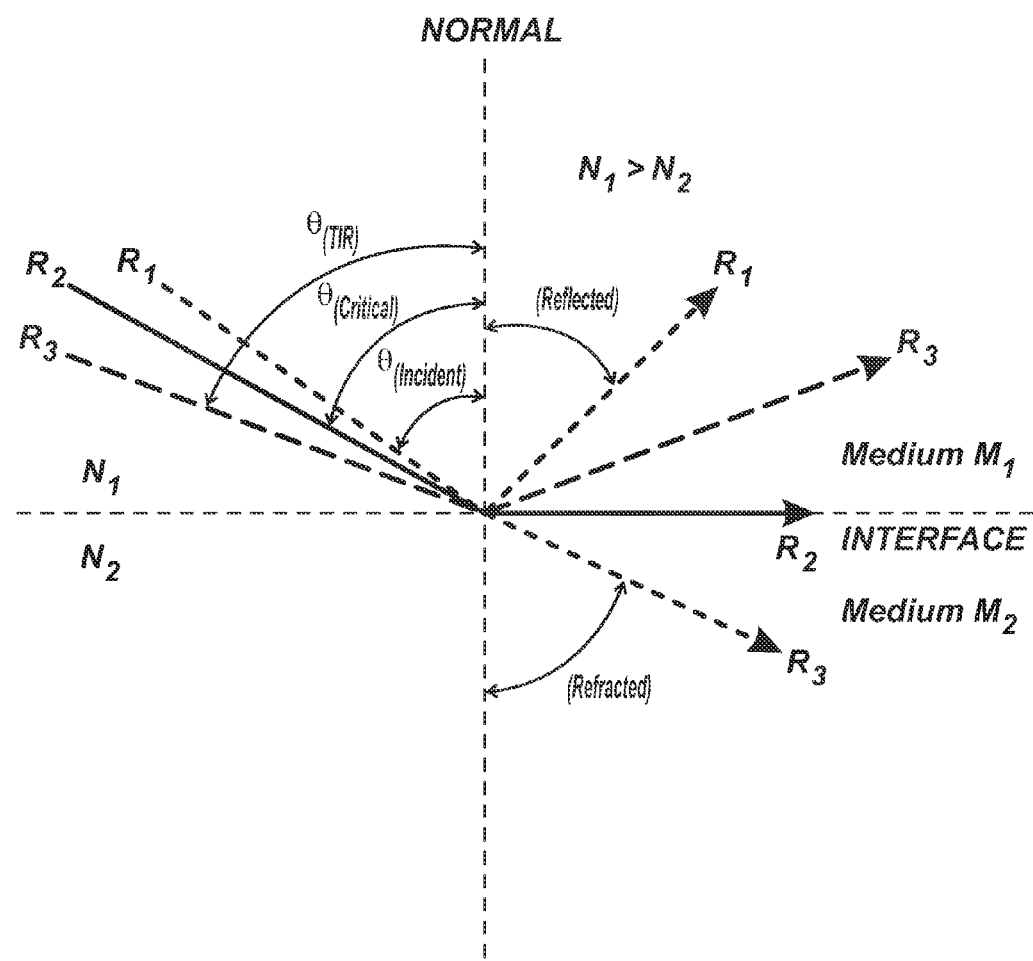
FIG. 1 illustrates light rays incident at different angles to an interface between two transparent mediums.
Figure 2:
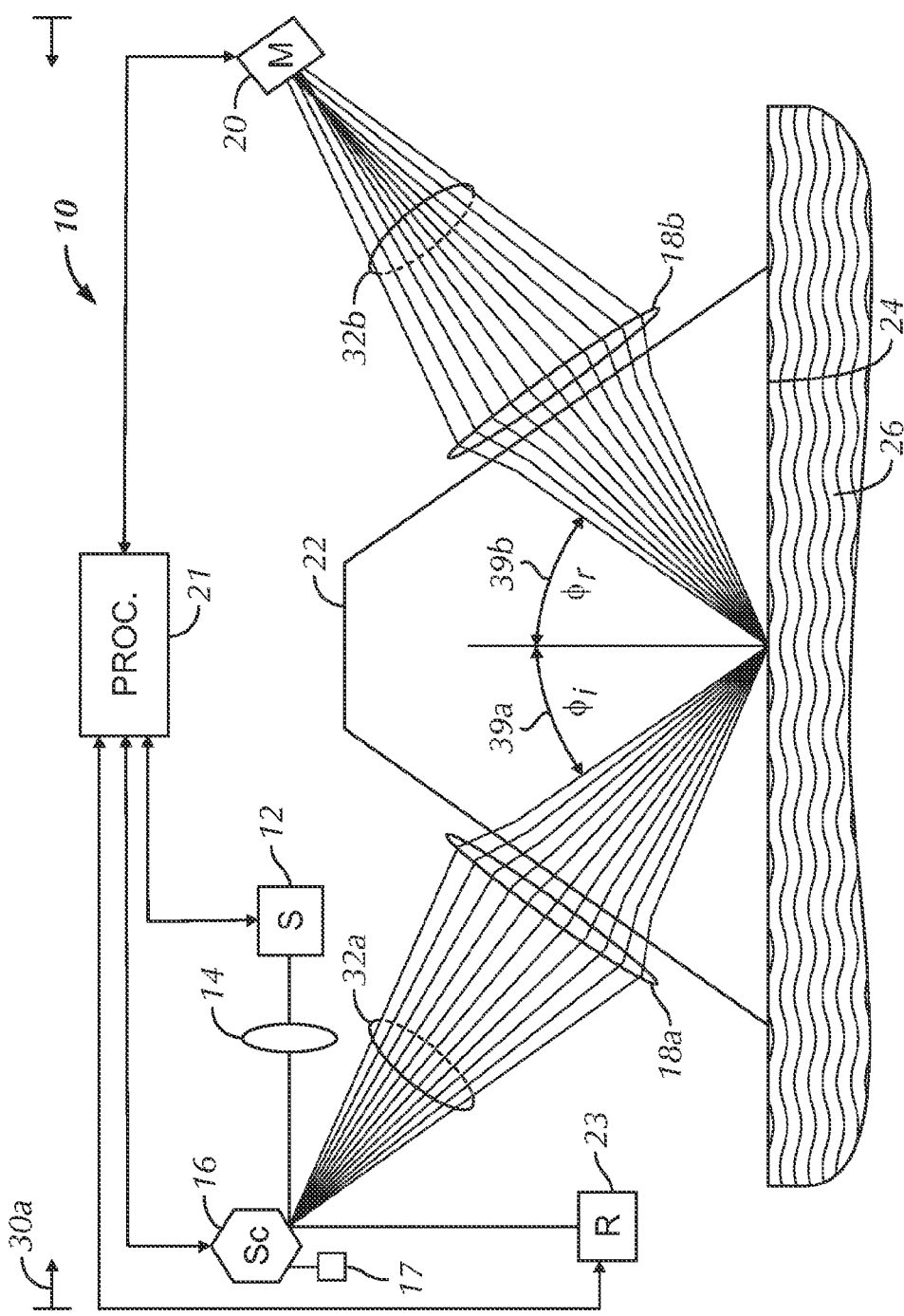
FIG. 2 illustrates a refractive index sensor according to certain teachings of the present disclosure.

Initial details of a refractive index sensor 10 for use in fluid analysis are illustrated in FIG. 2. The refractive index sensor 10 uses a critical angle approach to determine the refractive index of an unknown transparent medium 26 (e.g., fluid sample). The sensor 10 has a source 12, an adaptive optical element or scanner 16, lenses 18a-18b, a measurement detector 20, and a sensing optic 22. As it operates overtime, the sensor 10 measures the critical angle of the fluid sample 26 and determines the sample's refractive index $n_t$ continuously over time. Because it operates in the time domain, the refractive index sensor 10 is practically independent of the intensity of the source 12.

The source 12 emits an input signal (i.e., electromagnetic radiation) that passes through a collimation assembly 14 and then impinges upon the scanner 16. The source 12 can have one or more source elements for electromagnetic (EM) radiation and can use LEDs, Laser Diodes (LDs), or other types of sources. Moreover, the source 12 can be spectrally filtered and spatially shaped using one or more optical elements (either reflective, diffractive, or refractive in nature) and using techniques known in the art. The collimation assembly 14 can be a concave mirror or a collection of optical lenses and/or pinholes.

For its part, the scanner 16 in one implementation has a multi-sided scanning mirror with a motor or other actuator 17 that rotates or oscillates the mirror to provide multiple scanning angles. For example, the scanner 16 can have a two-sided flat mirror, and the actuator 17 can be a DC based motor having drive control electronics. Alternatively, the scanner 16 can be a Micro-Optical Electro-Mechanical System (MOEMS) driven by control electronics.

The source's input signal impinges the scanner 16 at a fixed angle so that the scanner 16 reflects the scanned signal at sequential angles as a function of time as the scanner 16 rotates or oscillates. Form the scanner 16, the scanned signal 32a is diagrammatically shown as reflecting at angles (conceptually indicated by ray paths) from the scanner 16, although the scanning may be more continuous with more angular definition.

A suitable input lens 18a at the input side of the sensing optic 22 then images the scanned signal 32a from the scanner 16 into the sensing optic 22. This lens 18a helps tailor the sensor 10 to the scan range of the scanner 16 and helps tailor the propagation length of the scanned signal 32a to fit the geometrical requirements of the sensing optic 22. For example, the lens 18a serves to focus the scanned signal 32a and can set the refractive index sensor 10 to operate in a predetermined measurable range of refractive indices. The lens 18a can be selected to fit the scanner's motion and desired angles in the sensing optic 22, and the lens' focal length can be selected to provide a desired propagation distance within the optic 22. The other lens 18b at the output side of the sensing optic 22 can be similarly configured.

As shown, the sensing optic 22 has a prism shape, although other shapes could be used to meet packaging requirements or to alter the measurement range of the sensor 10. For use with certain transparent mediums (such as downhole fluids), the sensing optic 22 is preferably composed of a material having an index of refraction greater than 1.45, and more preferably greater than 1.65 for downhole fluids, although other values may be used for different fluids. Some suitable materials for the optic 22 include sapphire, ruby, zircon, cubic zirconium, diamond, garnet, etc. For downhole use, the sensing optic 22 is preferably composed of sapphire with an index of refraction of about 1.70, which provides enhanced dynamic range for the sensor. In addition, a higher refractive index material such as diamond could also be implemented.

As shown, a portion of the optic's surface contacts the fluid sample 26 and forms a boundary or an interface 24 with the fluid sample 26. At this interface 24, the refractive index experienced by the scanned signal 32a changes from the optic's refractive index to the fluid sample's refractive index, which is different. As the scanner 16 scans the input signal from the source 12 and directs the scanned signal 32a sequentially in the time domain through the input lens 18a and through the sensing optic 22, the scanned signal 32a strikes the interface 24 at sequentially varying angles of incidence $\theta_i$ shown at 39a. As shown, the angular expanse of the scanned signal 32a translates to a wide range "i" of incident angles $\theta_i$ and therefore to a wide range of potential refractive indices $n_i$ for the unknown fluid sample 26.

As shown, a separate reference detector 23 may be optically coupled to the scanner 16 to receive a direct reference signal indicative of a time signature of the scanner's scan cycle, such as a start, end, or other consistent time of the scan cycle. In this way, portion of the scanned signal from the scanner 16 can travel to the reference detector 23 separate from the measurement detector 20. Among other purposes, the reference detector 23 can be used for timing purposes and to ensure that the source 12 is actually generating an input signal. As an alternative described later, portion of the scanned signal 32a can be reflected directly from the scanner 16 to the measurement detector 20 to be utilized as a scan rate reference of the sensor 10, rather than to a separate reference detector 23. Either way, the sensor 10 can readily determine the time signature (e.g., start time) of a scan cycle as the scanned signal 32a sweeps across the varying angles of incidence $\theta_i$. Additionally, either reference technique can allow the sensor 10 to verify that the source 12 is actually operating, which can reduce the chances making a false measurement.

Depending on the refractive properties of the fluid sample 26, one of the incident angles $\theta_i$ of the scanned signal 32a can be refracted at the critical angle parallel with the interface 24. Any incident signal 32a impinging the interface 24 at an angle beyond this critical angle will be reflected entirely in the sensing optic 22 at an angle of reflection $\theta_r$ shown at 39b. In such an instance, the corresponding angle of incidence $\theta_i$ from the angle of reflection $\theta_r$ would in fact be indicative of a critical angle $\theta_c$ for the fluid sample 26 being measured. Different fluid samples 26 would illicit different critical angles $\theta_c$ due to their different refractive indices relative to the refractive index of the sensing optic 22. The reflected signal 32b from the interface 24 emerges from the sensing optic 22 and passes through a suitable output lens 18b to the face of the detector 20.

As the scanned signal 32a interacts with the interface 24 at different angles of incidence $\theta_i$ over time, the detector 20 responds to the reflected signal 32b as a function of the critical angle $\theta_c$ at the interface 24 between the optic 22 and sample 26. Because the sensing optic 22 is part of the sensor 10, it has a known refractive index. The fluid sample 26, however, is not known and neither is its refractive index, although it is assumed to be different from that of the sensing optic 22. Based on the scan rate of the scanner 16 during a scan cycle, the values for the angles of incidence $\theta_i$ and any resulting angles of reflection $\theta_r$ are known based on the time that they occur in the scan cycle. Knowing this information, the time domain response at the detector 20 detecting the reflected signals 32b can be correlated to the refractive index of the unknown fluid sample 26. In turn, the material properties of the fluid sample 26 can be determined from this correlated refractive index.

A processor 21 cooperates with the detector 20 (and separate reference detector 23 if present) and the scanner 16. The processor 21 can record the response of the detector 22, the scan rate of the scanner 16, and various other parameters of the sensor 10 during operation. In turn, the processor 21 can determine the refractive index of the fluid sample 26.

As can be seen, the detector 20 is a fixed measurement point that is invariant to the refractive index, and Therefore, any inhomogeneity or phase separation in the fluid sample 26 can be determined by examining the responses of the detector 20 in real-time. For example, any slugging, emulsification, or the like in the flow of the fluid sample 26 would produce fluctuations in the index of refraction measurements. These fluctuations can be detected by the processor 21 to determine whether current flow of the fluid sample 26 is due to slugging, emulsification, etc.

As noted previously, the source 12 can have one source element (i.e., LED) generating the input signal. As an alternative, the source 12 can have two or more source elements (i.e., LEDs), and each can generate a different wavelength for the input signal. During operation, the processor 21 operatively coupled to the source 12 can selectively configure the wavelength for the input signal generated. In this way, the processor 21 can use a first wavelength at one point in time, followed by one or more wavelengths at another point in time by separately operating the source elements in the source 12. This can give the sensor 10 greater versatility during operation.

The width of the sensor 10 illustrated in FIG. 2 is conceptually indicated by 30a. The following section will illustrate how this dimension can be reduced and will illustrate additional components for the sensor 10 useful for analyzing fluid in a harsh environment, such as downhole in a well borehole.

B. Downhole Refractive Index Sensor

Figure 3:
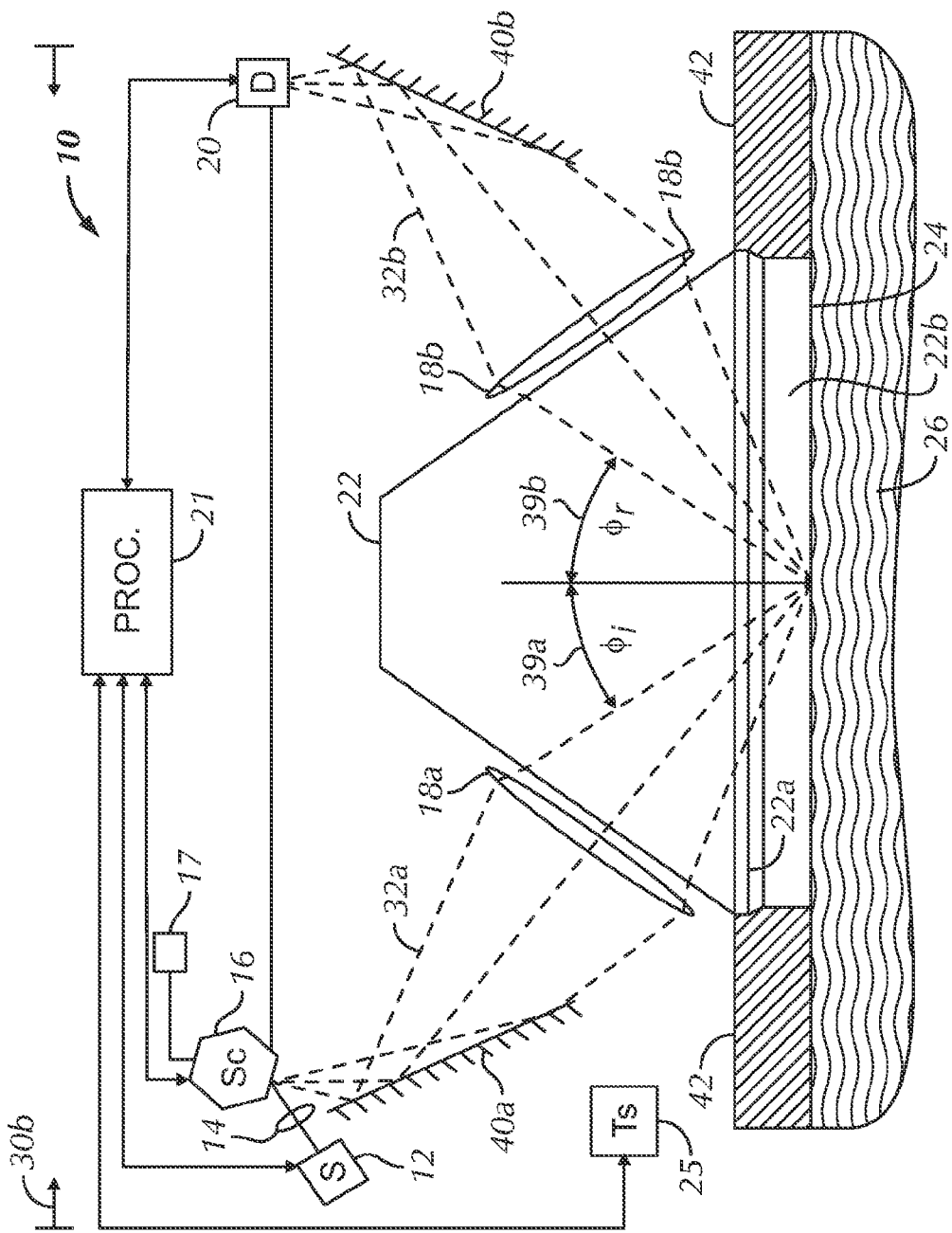
FIG. 3 illustrates an alternative arrangement for the refractive index sensor of FIG. 2.

In FIG. 3, an arrangement of the refractive index sensor 10, which is conceptually the same as illustrated in FIG. 2, is shown with some additional detail. In one such detail, FIG. 3 shows how the physical dimensions 30b of the refractive index sensor 10 can be reduced by using folding mirrors 40a-40b. As shown, the folding mirrors 40a-40b can reduce the required size of the entire sensor 10 by folding the signals 32a-32b so the sensor 10 can encompass a smaller package in a downhole tool, although use of folding mirrors 40a-40b may not be required for the sensor 10 to operate in a downhole tool. In addition to the mirrors, FIG. 3 shows additional components of the refractive index sensor 10 suitable for use downhole.

As before, the source 12 emits the input signal that passes through the collimator assembly 14, and the input signal impinges upon the scanner 16. In turn, the scanner 16 actuated by actuator 17 scans the input signal sequentially at a plurality of sequential angles as a function of time.

As shown, portion of scanned signal 32a can be reflected directly from the scanner 16 to the measurement detector 20 to be utilized as a scan rate reference of the sensor 10. In this way, the sensor 10 can readily determine the time signature (e.g., start time) of a scan cycle as the scanned signal 32a sweeps across the varying angles of incidence $\theta_i$. Additionally, using the direct signal from the scanner 16 to the detector 20, the sensor 10 can verify that the source 12 is actually operating, which can reduce the chances of making a false measurement.

From the scanner 16, the scanned signal 32a reflects off the fold mirror 40a, and the input lens 18a images the scanned signal 32a into the sensing optic 22. Once again, a portion of the optic's surface contacts the fluid sample 26 to form an interface 24 with the fluid sample 26. In the current arrangement, the sensing optic 22 includes a shoulder 22a and a plateau 22b that serve to provide a high-pressure and high-temperature liquid tight seal for insertion of the optic 22 into a fluid sampling device, which typically has a flow line with a wall 42 or the like.

As before, the scanned signal 32a impinges upon the interface 24 at sequentially varying angles of incidence $\theta_i$ shown at 39a, and the reflected signal 32b can be reflected at corresponding angles of reflection $\theta_r$ at 39b depending on the refractive index of the fluid sample 26. This reflected signal 32b emerges from the sensing optic 22 and passes through the output lens 18b to the opposing fold mirror 40b and subsequently to the face of the detector 20.

In comparing the dimension 30a of FIG. 2 with the dimension 30b of FIG. 3, it can be seen that the width of the refractive index sensor 10 has been reduced by using the folding mirrors 40a-40b to route the signals in FIG. 3. In addition to the folding mirrors 40a-40b, other techniques for routing signals known in the art can be used to reduce the dimension of the refractive index sensor 10. In one implementation of the sensor 10, the deflection of the folding mirrors 40a-40b can be about ±10°, the incidence angles $\theta_i$ at the interface 24 can be about $34.6° \leq \theta_i \leq 69.6°$, and the measurable refractive index range (n) can be about $1.00 \leq n \leq 1.65$ when using a sapphire sensing optic 22.

Operation of the refractive index sensor 10 is similar to that discussed previously. Yet, the refractive index of the sensing optic 22 for use in a harsh environment is preferably well characterized at elevated temperatures. As is known, the refractive indices $n_i$ of a given material i is temperature dependent. Therefore, the sensor 10 preferably correlates temperature and the refractive index of the unknown fluid sample 26. To accurately measure temperature, the refractive index sensor 10 can have a built in thermal sensor 25 that cooperates with the processor 21. Using temperature measurements from the sensor 25, the processor 21 can then use the known refractive index of the sensing optics 22, the temporal sensor response from the unknown fluid sample 26, and other environmentally dependent variables of the system to minimize inaccuracies in the prediction of fluid properties or composition.

In addition to temperature dependence, the refractive index $n_i$ of the fluid sample 26 can depend on the wavelength ($\lambda$) of the signal used from the source 12. In a typical installation for use in a downhole environment, the refractive index sensor 10 may be operated at a measurement wavelength $\lambda$ (the wavelength emitted from the source 12) of about 760 nanometers (nm). However, the measurement range and/or dynamic range of the sensor 10 can be changed by altering what wavelength is used. Therefore, the source 12 can use a plurality of sources and/or filters to produce signals at different wavelengths so the sensor 10 can have a wide, selectable measurement range. Thus, the processor 21 in some implementations can select the wavelength of interest to be emitted by the source 12 and used by the sensor 10.

C. Detector Details

Figure 4A:
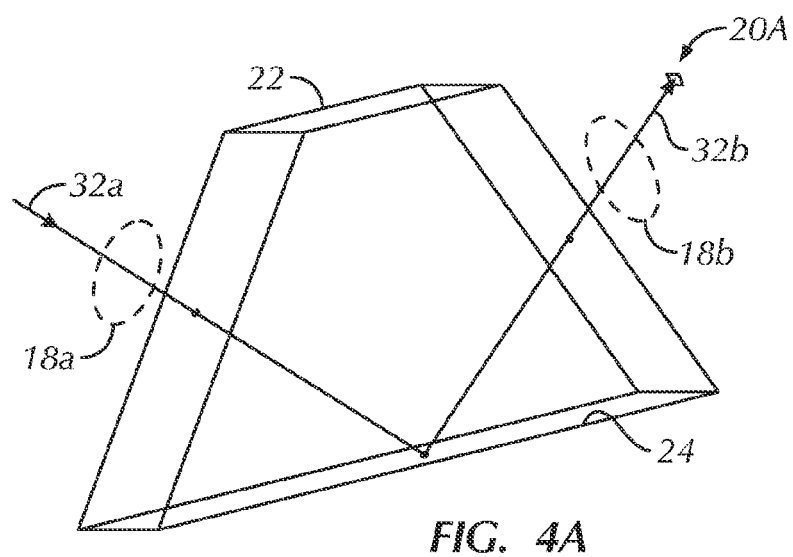
FIGS. 4A-4B show two signal path arrangements for the refractive index sensor.

In general, the detector 20 for the refractive index sensor 10 disclosed herein can be a single-element photodiode, a multi-element photodiode, an avalanche photodiode, a photomultiplier tube, a micro-channel plate, a bolometer, and/or a thermopile and can have any suitable detector material (e.g., Si, InGaAs, PbS, PbSe, MCT, etc.). As shown in FIG. 4A, the incident signal 32a for the sensor 10 may be a focused beam passing from the source/scanner (not shown) and through the lens (schematically indicted at 18a) to interact with the interface 24 of the optic 22. This incident signal 32a can come from a single element source or from a multiple element source with proper spatial shaping. If total internal reflection is occurring, the reflected signal 32b passes out of the optic 22, through the other lens (schematically indicated at 18b), and to the detector 20A. As shown here, this detector 20A is a single photodiode element.

Figure 4B:
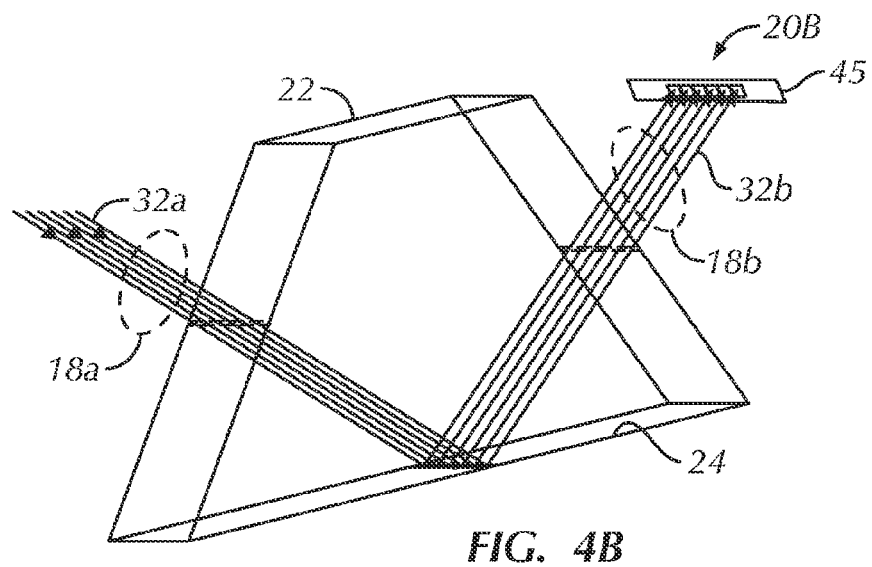

As shown in FIG. 4B, however, the incident signal 32a may be a wide beam (shown as a span of rays) passing from the source/scanner (not shown) and through the lens (schematically indicted at 18a) to interact with the interface 24 of the optic 22. Again, this incident signal 32a can come from a single element source or from a multiple element source with proper spatial shaping. If total internal reflection is occurring, the reflected signal 32b passes out of the optic 22, through the other lens (schematically indicated at 18b), and to the detector 20B. As shown here, this detector 20B can be an array of single detectors or can be a diode array. To avoid disparities in temperature effects, the array of single detectors can be packaged together, or the diode array may use a thermoelectric (TEC) cooler 45 to control temperature differences.

In the present arrangement, the detector array 20B is not oriented for detection of multiple angles of incidence. Rather, the detector 20B senses the wide beam of the reflected signals 32b at the sequential angles past the critical angle so the detector 20 can monitor a larger interface region. This, in turn, can improve measurement sensitivity and can provide built in detection redundancy. Additionally, the detector 20B with the array can be used to detect multiple wavelengths simultaneously as noted elsewhere herein, especially when the source of the incident signal 32a has multiple elements of different wavelengths.

In yet another alternative, the signal may be a wide beam as in FIG. 4B, but the lens 18b and other optical elements may direct the wide signal passing from the sensing optic 22 to a point where it is detected by a single detector. These and other arrangements are also possible for the detector 20 of the sensor 10.

D. Detector Response

Figure 5:
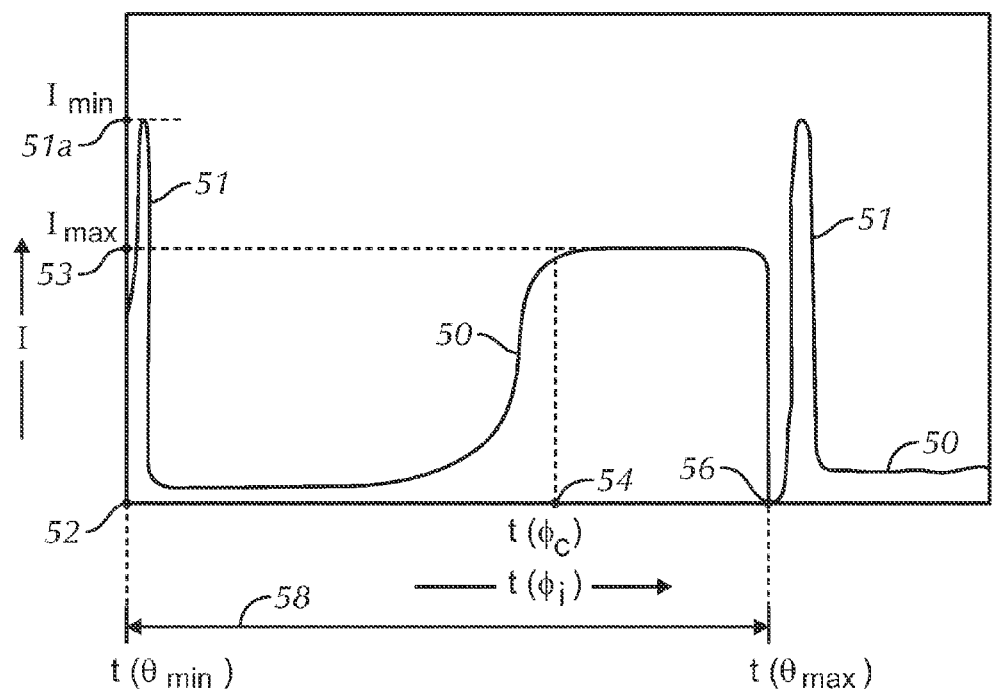
FIG. 5 conceptually illustrates a response of a detector in the disclosed refractive index sensor.

With an understanding of the sensor 10's components and operation, discussion now turns to FIG. 5 conceptually showing response of the detector (20) in FIGS. 2 and 3. (To facilitate description, reference numerals for components in FIGS. 2 and 3 will also be used.) The curve 50 represents the response (Intensity "I") of the detector (20) (ordinate) as a function of the scan time $t(\theta_i)$ (abscissa). The scan time $t(\theta_i)$ corresponds to the angle of incidence of the scanned signal (32a) from the scanner (16) at the optic's interface (24). Accordingly, the detector's response is measured in the time domain and is, in turn, a function of the angle of incidence $\theta_i$. Therefore, the intensity I of the reflected signal (32b) impinging upon the detector (20) is measured as a function of time $t(\theta_i)$. The illustration in FIG. 5 assumes that the input signal as it is scanned by the scanner (16) goes from a small incident angle $\theta_i$ to a large incident angle $\theta_i$.

As noted previously, a portion of the scanned signal (32a) from the scanner (16) can be reflected directly to the detector (20) to indicate the start of the scan cycle as in FIG. 3. Thus, the start of the scan cycle is denoted at time $t(\theta_{start})$ at 52 by an optical timing pulse 51 of intensity $I_{start}$ shown at 51a, and the scan cycle terminates at a time $t(\theta_{stop})$ shown at 56. If a separate detector 23 is used as in FIG. 2, then the intensity measured by this detector 23 can indicate the start of the scan cycle.

During the scan cycle of duration $(t(\theta_{start})-t(\theta_{stop}))$ shown at 58, the angle of incidence $\theta_i$ increases and approaches a critical angle of the interface (24). At the critical angle, the detected signal's intensity rises rapidly to a value $I_{max}$ shown at 53 at a time $t(\theta_c)$ indicated at 54, since all of the incident signals beyond the critical angle are reflected at the interface (24) and contained within the sensing optic (22). This elevated detector response $I_{max}$ continues as the angle of incidence $\theta_i$ further increases beyond the critical angle $\theta_c$. Finally, the detector response $I(\theta)$ terminates at the end of the scan cycle $t(\theta_{stop})$, at which point the scan cycle is then repeated with a new start pulse 51.

As the curve 50 indicates, the critical angle $\theta_c$ at the interface (24) between the sensing optic (22) and the fluid sample (26) has a unique time domain signature $t(\theta_c)$ at the detector (20) that is a function of the scan rate and the angular divergence of the source. Utilizing this time domain signature $t(\theta_c)$ in combination with the scan rate of the signal (32a), the angular divergence of the collimated signal, and the refractive index of the sensing optic (22), the refractive index $n_i$ of the unknown fluid sample (26) can be calculated. As noted above, the time domain signature $t(\theta_c)$ at which the critical angle $\theta_c$ occurs is determined from the detector response in the time domain. Thus, the critical angle $\theta_c$ is determined directly from this measured time domain signature $t(\theta_c)$ because the scan rate and the angular divergence of the input signal (32a) are already known for the sensor (10).

The refractive index sensor (10) makes all of its scan measurements in the time domain and does not use the absolute intensity values of the detector responses. By operating in the time domain, the sensor (10) can avoid problems with sensitivities in the sensor (10) caused by analog drift in the support electronics, dark current fluctuations within the detector (20) due to environmental (i.e., temperature) changes, and/or fluctuations in the source (12). All of these perturbations would lead to errors in any conventional intensity based optical sensor.

In another implementation, however, the sensor (10) can use cooling to cool the components and to minimize dark current drift and/or analog circuitry drift, although it may not alleviate source drift. Use of dynamic cooling in a downhole environment must be compatible with available power budgets and should be able to establish a suitable thermal differential with the external environment. Yet, in preferred implementations, the sensor (10) does not need to be cooled to obtain accurate and precise measurements, and the resolution and sensitivity of the sensor (10) even when used downhole is expected to approach that of laboratory instrumentation.

E. Determining Refractive Index and Other Properties

As described above, the response of the detector 20 provides the critical angle $\theta_c$ for the interface 24 between the fluid sample 26 and sensing optic 22. From this critical angle $\theta_c$, the refractive index $n_i$ of the fluid sample 26 can be determined. At this point, additional details may be considered once the refractive index $n_i$ of the fluid sample 26 has been determined.

One consideration involves the influence of temperature on the sensor 10 and the resulting refractive index determined. As noted previously, the refractive index of the sensing optic 22 is well characterized even at elevated temperatures. Therefore, the refractive index $n_i$ of the sample's unknown material can be determined directly from the measured critical angle $\theta_c$ (i.e., that angle occurring at a determinable point in time slightly before the signal reflects off the interface 24, stays internal the optic 22, and is measured by detector 20). Because the sensor 10 can have an integrated thermal sensor 25 (FIG. 3), this determined refractive index $n_i$ can then be correlated to standard conditions in many instances using a measured temperature T from the sensor 25 and using correlation information in a look up table, formula, or the like.

Another consideration involves how the processor 21 or other controller process data, especially when used downhole. The processor 21 is preferably preprogrammed to control operation of the source's components (i.e., source 12 and/or adaptive optical element 16), to analyze the response of the detector 20, and to compute the desired refractive indices $n_i$. Processing by the processor 21 or other controller can determine characteristics of the fluid sample 26 based on its determined refractive index.

Briefly, the refractive index of the unknown sample is measured. Subsequently, the measured refractive index is processed using an equation, analytical model or an empirical model to predict specific fluid properties. For example, the processor 21 or other controller can determine one or more characteristics associated with the sample using the determined refractive index. In general, the determined characteristic can include, but is not limited to, an indication of an environmental condition (e.g., pressure, temperature, etc.) of the sample, a chemical composition of the sample, presence of gas in the fluid sample, presence of emulsified material in the fluid sample, or presence of slug flow in the fluid sample.

Along these lines, one consideration involves determining the constituents of the fluid sample 26 based on the determined refractive index. As is known, the refractive index of a mixture of components is typically the sum of the weighted average for the refractive indices of each component. Through empirical or derived methods, component concentrations can thereby be predicted from the refractive index data obtained from the mixture. Any data from such empirical or derived methods can be stored at the processor 21 or other controller in the form of a look up table, equation, etc. so the processor 21 can characterize the fluid mixture based on the determined refractive index of the fluid sample 26 being analyzed.

F. Adaptive Optical Element

As noted previously in FIGS. 2 and 3, the adaptive optical element 16 of the disclosed sensor 10 can be a scanning mirror or other adaptive optical element, such as a Liquid Crystal on Silicon (LCoS) element, or a Micro-Electro Mechanical System (MEMS) micro-mirror, also know a Micro-Optical Electro-Mechanical System (MOEMS) elements.

Figure 6:
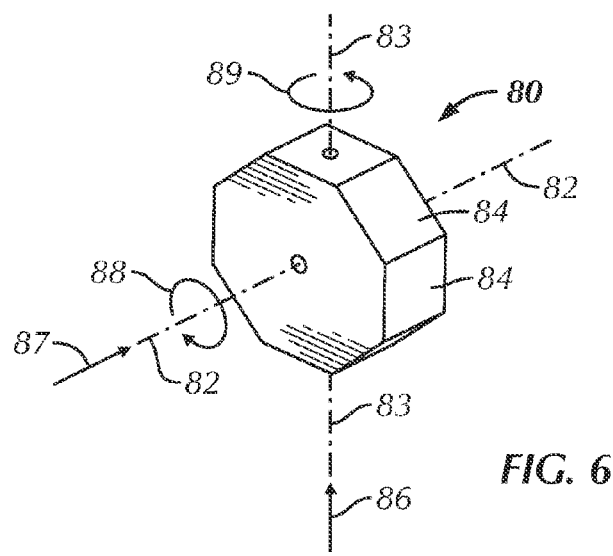
FIG. 6 is a perspective view of a scanning mirror for the disclosed refractive index sensor.

FIG. 6 shows a spinning mirror 80 that can be used for the disclosed scanner 16. This spinning mirror 80 has eight mirrored surfaces 84 disposed about its periphery. If the mirror 80 is rotated about an axis 82 as indicated conceptually by the arrow 88, an impinging signal 86 will reflect off of the eight mirrored surfaces 84 (two denoted), thereby giving eight sweeps per revolution of the mirror 80. Alternately, if the mirror 80 is rotated about an axis 83 as indicated conceptually by the arrow 89, an impinging signal 87 will reflect off two mirrored faces 85, thereby giving two sweeps per revolution of the mirror 80.

For a given mirror rotation speed, resolution in the time domain would be four times greater if the mirror 80 is rotated as an eight surface mirror about the axis 82. There are, however, certain operational advantages to rotating a two surface mirror about the axis 83. Although an eight or two surface arrangement of the scanning mirror 80 is depicted, it should be understood that sensor 10 can use a single surface mirror or a mirror having more or less than eight surfaces. In addition, the mirror 80 can have reflecting surfaces with unequal angles relative to the source 12's axis. In this way, the rotating mirror 80 with sides at different angles can create a series of unique temporal signals 50 per mirror revolution. The different temporal plots produced for the same refractive index may then help with signal resolution.

The scanning mirror 80 is rotated with a motor or other actuator, which is not shown for brevity and clarity. If the scanning mirror 80 is rotated at a rate of about 370 rotations per second, the disclosed refractive index sensor 10 will achieve about 370 scans per second per reflecting surface, or 2960 scans per second, which may be a suitable time resolution for most applications. Using such a multi-sided mirror 80 may decrease available temporal resolution, but the mirror 80 can increase the measurement frequency and thus signal averaging, which can improve measurement stability and reliability. The multi-sided mirror 80 may also increase the number of snap-shots in time and may lead to improved understanding of non-homogeneous flows of the fluid sample.

G. Sensing Optic

Figure 7A:
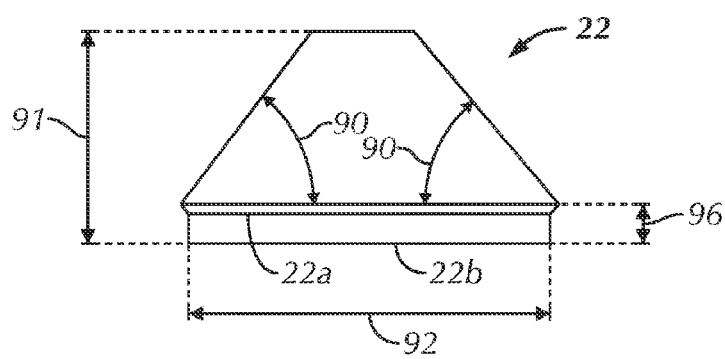
FIGS. 7A-7B depict side and bottom views of a sensing optic for the disclosed refractive index sensor.
Figure 7B:
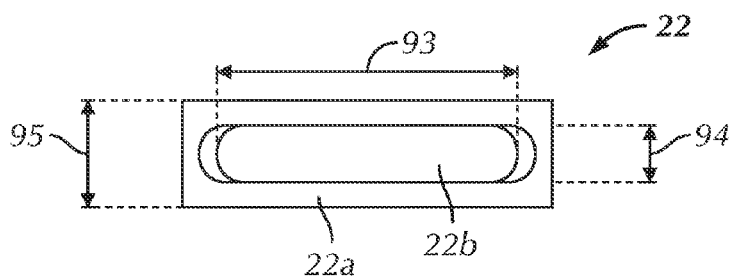

Details of the sensing optic 22 suitable for use in the disclosed refractive index sensor 10 are shown in FIGS. 7A-7B. In one implementation, the sensing optic 22 has a prism shape as shown and is composed of sapphire having an index of refraction of about 1.70. Overall, the optic 22 is configured so that a given refractive index measurement range of interested can be measured. This requirement establishes what ratios of height 91, length 92, and width 95 may be required to yield prism angle 90. As mentioned previously, other shapes of the sensing optic 22 can be used while still maintaining the basic operating concepts of the disclosed refractive index sensor 10.

H. Housing for Refractive Index Sensor

Figure 8:
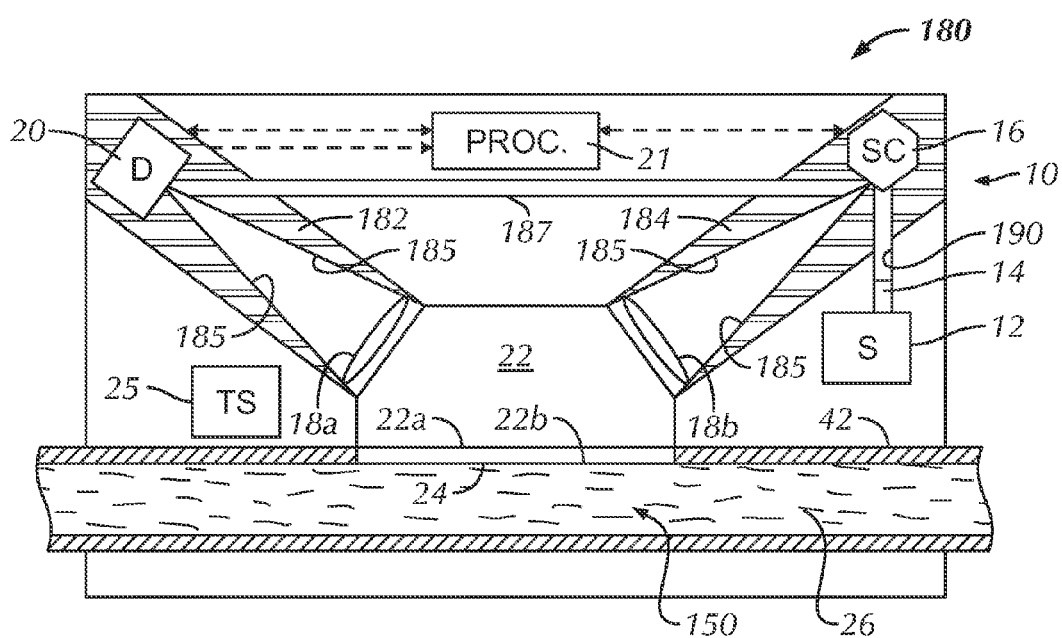
FIG. 8 shows a housing arrangement for the disclosed sensor for use in a section of a downhole tool.

The disclosed refractive index sensor 10 can be disposed in a housing that, in turn, can be disposed in a host device. In general, this host device can be a laboratory device, industrial monitor or a downhole tool, such as a formation tester, used in wellbore exploration. As shown in FIG. 8, a housing 180 (only a portion of which is shown) for the refractive index sensor 10 holds the source 12, the collimator assembly 14, the scanner 16, the lenses 18a-18b, the detector 20, and the sensing optic 22. For downhole use, the housing 180 is preferably small and rugged and can operate in a temperature range of −20° C. to 200° C., although such requirements may not be necessary for a laboratory device.

As shown, the housing 180 positions next to a flow line 150 (only a portion of which is shown) of the host device through which the fluid sample 26 passes to be tested by the refractive index sensor 10. Most of the sensor 10 can be symmetrically arranged in the housing 180, which can facilitate fitting the sensor 10 in the host device.

An input corridor 190 in the housing 180 optically couples the source 12 to the scanner 16. A motor or other actuator operating the scanner 16 is not shown. The scanner 16 is mounted within one corridor 184 that communicates with the input side of the sensing optic 22, and the detector 20 is mounted within another corridor 182 that communicates with the output side of the sensing optic 22. A cross corridor 187 interconnects the two corridors 182 and 184 to communicate a direct signal reflected from the scanner 16 to the detector 20 to indicate the start time of the scan cycle ($t_{start}$).

The sensing optic 22 is optically coupled to the flow line 150 through which the unknown fluid sample 26 flows. The sensing optic 22 is hermetically sealed to the wall 42 of the flow line 150 by the previously mentioned shoulder 22a and plateau 22b. The interface 24 is preferably disposed flush with the wall 42 of the flow line 150.

The processor 21 may or may not be housed in the housing 180 with the other components. However, the processor 21 is operationally coupled to the scanner 16, the detector 20, and the temperature sensor 25 as conceptually indicated with broken lines. The processor 21 is preprogrammed to determine the time $t(\theta_c)$ from the response of detector 20 as illustrated graphically by the curve 50 in FIG. 5. The processor 21 is also preprogrammed to monitor the scan rate of the scanner 16, store the predefined angular dispersion of the scanned signal that the scanner 16 produces in the optic 22, and combine these parameters to determine the critical angle $\theta_c$ based on the detector 20's response.

In one implementation, the processor 21 can send measured data to a controller of a host device (e.g., downhole tool) to complete calculations or send the measured data elsewhere for processing. Alternatively, the processor 21 can be preprogrammed to directly compute the refractive index $n_i$ for the fluid sample 26 flowing within the flow line 150 using the measured data. In addition, the processor 21 can use the response of the temperature sensor 25 to correlate the measured refractive index $n_i$ to standard conditions. Finally, the processor 21 can also be preprogrammed to include effects of the wavelength λ in the computation of refractive index $n_i$ and can control operation of the source 12 to selectively set a wavelength for the input signal depending on the implementation.

I. Downhole Tool Having Refractive Index Device

Figure 9A:
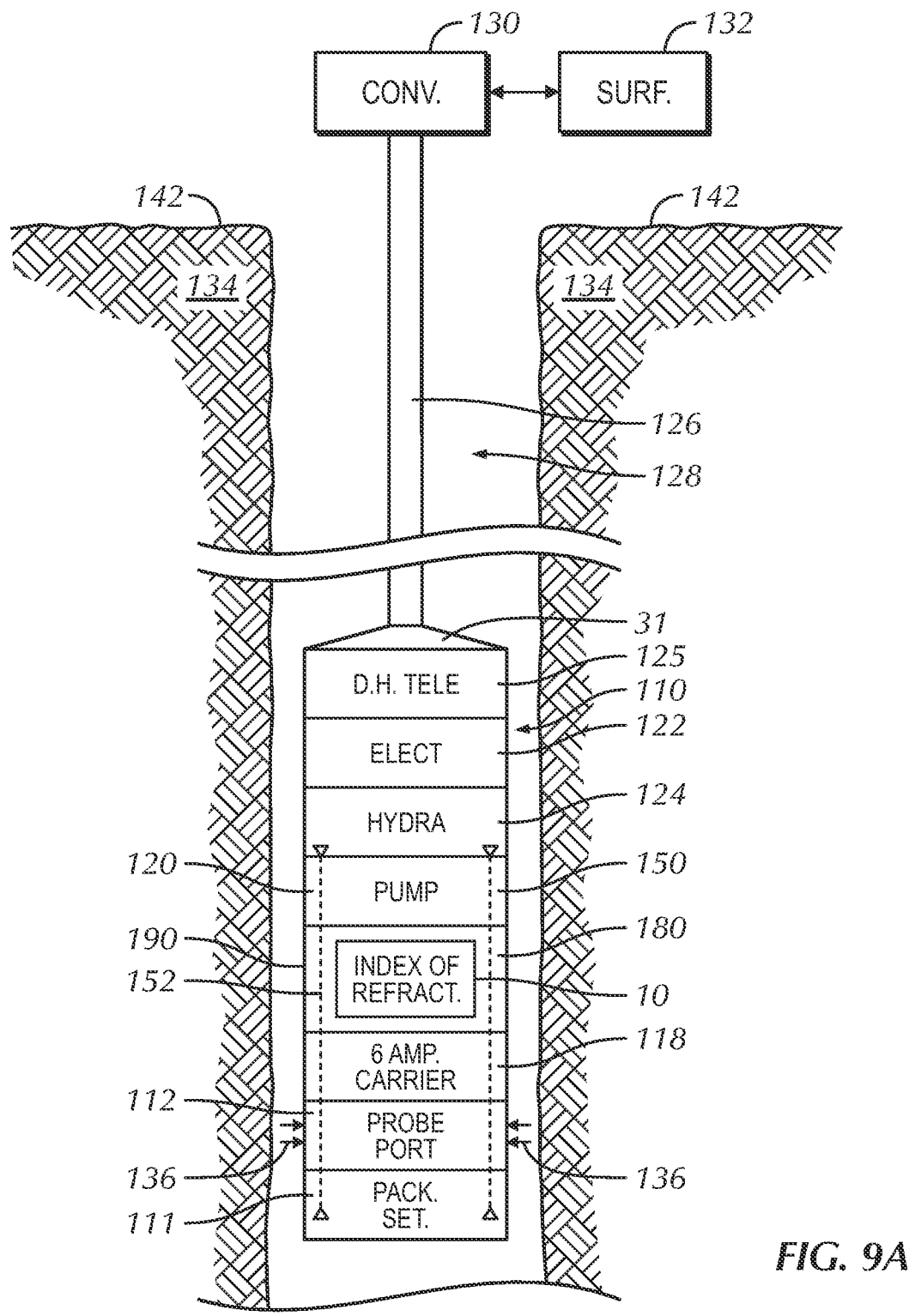
FIG. 9A conceptually illustrates a formation tester tool disposed in a borehole environment of a well and having a refractive index sensor of the present disclosure.

As shown in FIG. 9A, the disclosed refractive index sensor 10 can be used in a downhole tool 110 that operates in a well borehole 128 penetrating an earth formation 134. In one implementation, the downhole tool 110 is a formation tester, such as a wireline formation tester or drilling formation tester, and can be a formation tester such as disclosed in U.S. Pat. Pub. No. 2008/0173083, filed 24 Jan. 2007, which is incorporated herein by reference.

As shown, a conveyance apparatus 26 at the surface deploys the formation tester tool 110 downhole using a tubular, a cable, a wireline, or similar component 24. In general, the formation tester tool 110 can be conveyed along the borehole and can collect and analyze fluids from the formation to determine major constituents within the fluid either by stopping and pumping from an isolated zone in a borehole, by using production logging techniques known in the art, or by using some other available technique.

The formation tester tool 110 typically has operationally connected sections including a packer section 111, a probe or port section 112, a sample carrier section 118, a fluid analysis section 190, a pump section 120, a hydraulics section 124, an electronics section 122, and a downhole telemetry section 125. Dual fluid flow lines 150/152 extend through the sections of the tool 110 and are functionally configurable. However, other types of formation tester tools could also be used, such as those having a single flow line.

In operation, the probe section 112 having an intake port draws fluid into the tool 110. To isolate the formation fluid samples from contaminates in the annulus, the tool 110 can use isolation elements, such as packers of section 111 or other devices, to isolate a region of the formation. The pump section 120 then pumps collected fluid from the probe section 112 into the tool 110 via the flow lines 150/152. The fluid, which can contain hydrocarbon components (solid, liquid, and/or gas) as well as drilling mud filtrate or other contaminants, flows through the tool 110, and various instruments and sensors in the tool 110 analyze the fluid. For example, the measurement section 114 can have sensors that measure various physical parameters (i.e., pressure, temperature, etc.) of the fluid.

The fluid analysis section 190 has a housing 180 with the disclosed refractive index sensor 10 optically coupled to the flow line 150 (See e.g., FIG. 8). The refractive index sensor 10 can determine physical and chemical properties of oil, water, and gas constituents of the downhole fluid sample passing through the flow line 150. The processor 21 can be disposed in the fluid analysis section 190 as part of the sensor 10 as shown in FIG. 8, although a processor located elsewhere in the formation tester tool 110 can alternately be used to perform the previously discussed index of refraction calculations.

Eventually, fluid directed via the flow lines 150/152 can either be purged to the annulus or can be directed to the sample carrier section 118 where the samples can be retained for additional analysis at the surface. Hydraulic components 124 of the tool 110 can hydraulically operate valves and other elements within the tool 10, electronics section 122 can provide control and power to various electronics, and can communicate data via wireline or fluid telemetry to the surface. Uphole, surface equipment 132 can have a surface telemetry unit (not shown) to communicate with the downhole tool's telemetry components. The surface equipment 132 can also have a surface processor (not shown) that performs additional processing of the data measured by the tool 10.

Figure 9B:
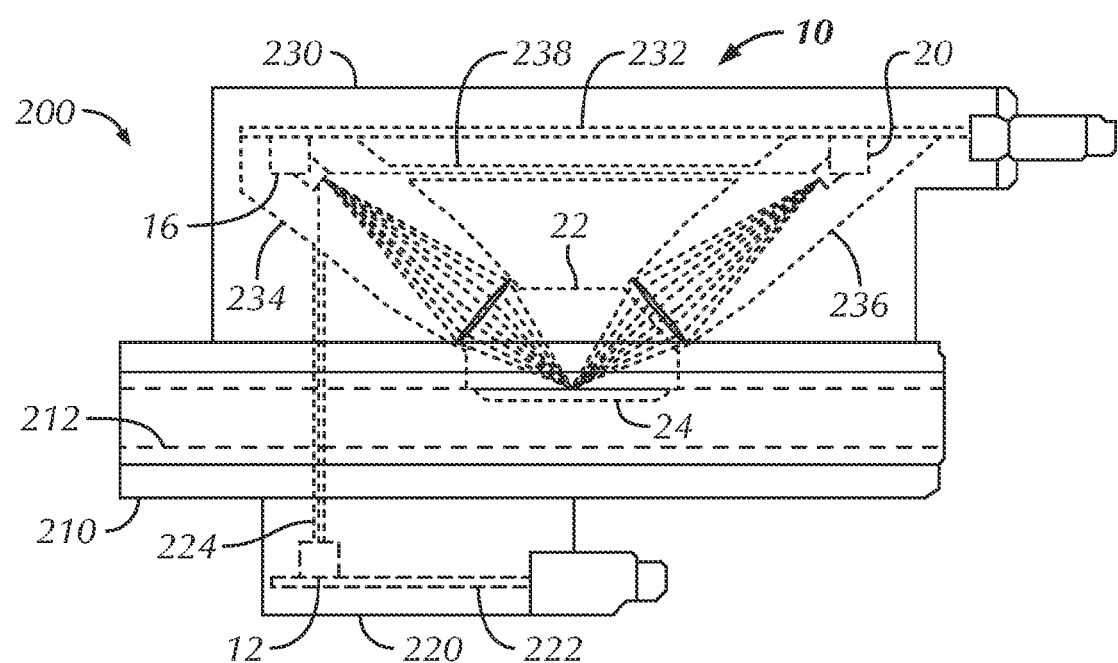
FIG. 9B shows an arrangement of the disclosed sensor disposed relative to a flow tube of a formation tester tool.

FIG. 9B shows an arrangement 200 of the disclosed sensor 10 disposed relative to a flow body 210 for such a formation tester tool 110 of FIG. 9A. For use in the downhole tool, the flow body 210 fits onto a tool chassis (not shown) that holds the flow body 210 in place and holds required electronics. In turn, the flow body 210 mates with a subassembly (not shown) that routes the flow buses in the downhole tool, and the tool chassis fits inside a tool housing (not shown) of the downhole tool. Fluid from one of the tool's fluid buses passes through a flow passage 212 from one end of the flow body 210 to the other and passes by the sensor 10's components.

As shown, a source unit 220 affixes to the flow tube 210 and has a circuit board 222 with one or more source elements (such as LEDs) of a source 12 and other necessary electronics. (Details related to imaging input signals from multiple LEDs and selectively configuring a wavelength of an input signal can be found in copending U.S. patent application Ser. No. 12/613,700, which is incorporated herein by reference). This unit 220 can have any other necessary optical shaping mechanisms—i.e., collimator, lens, etc. A detector unit 230 also affixes on the flow body 210 and has a circuit board 232 with a scanner 16, a detector 18, and any other necessary electronics.

The sensing optic 22 fits into a space defined in the unit 230 and disposes with its interface surface 24 interfacing with the flow passage 212 in the flow body 210 using appropriate sealing techniques. Signals for the source 12 pass through a cross-corridor 224 to the scanner 16 disposed in a another corridor 234 and on the circuit board 232. Because the cross-corridor 224 does not pass through the flow passage 212, it may be offset from the passage 212, may use beam routers such as mirrors and the like, or may use any other appropriate arrangement. From the scanner 16, a direct scanned signal passes through another cross-corridor 238 to the detector 20 disposed on the circuit board 232. Likewise, scanned signals pass at sequential angles to the optic 22, impinge the interface 24 and either are or are not reflected to the detector 20 disposed in the opposing corridor 236.

The arrangement 200 disclosed in FIG. 9B for the sensor 10 and flow body 210 is meant to be illustrative of when the sensor 10 is used with a formation tester or other downhole tool such as discussed in FIG. 9A. It will be appreciated that the components can be rearranged as needed based on space requirements, size of flow body, size of sensor 10' components, etc.

Although disclosed used in a formation tool 110, the refractive index sensor 10 can be deployed in any suitable tool used for wireline formation testing, production logging, Logging While Drilling/Measurement While Drilling (LWD/MWD), or other operations. Therefore, the downhole tool 110 can be a wireline formation tester, a drilling formation tester, a production logging tool, or other temporary, permanent, or semi-permanent tool to take fluids from the borehole. In fact, the tool 110 can even deploy in a side pocket mandrel, for example, for a gas lift system or the like.

J. Other Host Devices Having Refractive Index Device

Although the sensor 10 has been discussed in FIGS. 9A-9B for use in a downhole tool as the host device, the disclosed sensor 10 and techniques described herein can be used in variety of host devices, including laboratory instruments, industrial monitors, process monitors, or environmental monitors. For example, FIG. 10A conceptually illustrates a laboratory instrument 300 having an embodiment of the disclosed sensor 10.

Figure 10A:
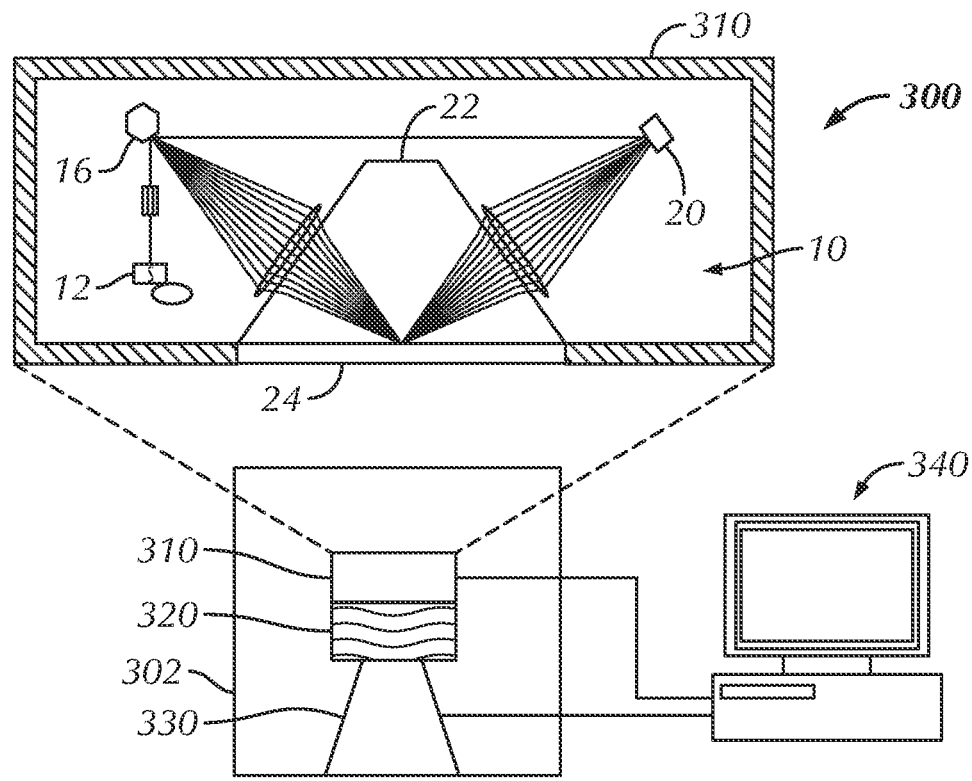
FIG. 10A conceptually illustrates a laboratory instrument having a refractive index sensor of the present disclosure.
Figure 10B:
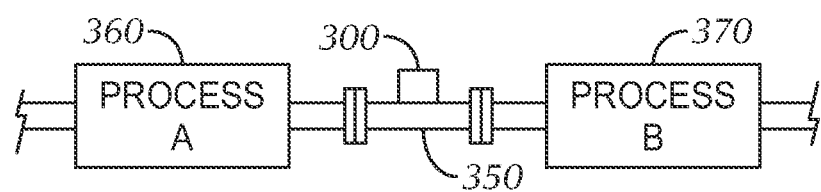
FIG. 10B shows the refractive index sensor used in a piping system of an industrial application.

As shown in FIG. 10A, the laboratory instrument 300 can have a housing 302, body, chassis, or the like, and the housing 302 can hold an instrument chamber 310 for the sensor 10 and a sample chamber 320 for the fluid sample to be analyzed. A processing device 340 (namely a computer or the like) couples to the instrument housing 302 and operates and monitors the instrument 300 to analyze the sample fluid.

The instrument chamber 310 houses most of sensor 10's components, while the sample chamber 320 houses a fluid sample. These two chambers 310/320 may be environmentally isolated from one another except for the interface 24 between the sensing optic 22 and the sample chamber 320. Although the instrument chamber 310 may remain closed to the environment, the sample chamber 320 may be opened to the atmosphere to facilitate changing samples and may actually include a flow tube to bring samples to the sensing optic 22.

Sample fluid is preferably transported or loaded in the sample chamber 320 without contaminating the instrument chamber 310's environment. Because the instrument 300 is not used in a harsh environment and the fluid may not necessarily be of high pressure or temperature, details related to sealing the optic 22 and otherwise making the sensor 10 robust to withstand a harsh downhole environment can be eliminated or less stringently applied in the laboratory instrument 300.

To actually transport fluid samples to and from the sample chamber 320 for analysis, the instrument 300 can have a fluid transport mechanism 330. This mechanism 330 can use pumps, vacuums, tubing, mechanical devices, or any of the available means to load fluid to and from the chamber 320 so that the sensing optic 22 can interface with the sample. Depending on the transport mechanism 330 used, the sample chamber 320 can be configured to hold a static fluid sample, move the sample through a flow line, or the like.

The instrument 300 of FIG. 10A can be a stand-alone device or can be integrated with another process and/or environmental monitor. As one brief example, FIG. 10B shows the instrument 300 (or at least a portion thereof) incorporated into a piping system 350 of an industrial application between two processes 360/370, although the instrument 300 can be incorporated in any suitable manner known in the art. Rather than having a sample chamber 320 and transport mechanism 330, the instrument 300 can have a flow bus or passage that diverts flow between the processes 360/370 from the piping 350 interconnecting them.

In the context of this disclosure, "sequential" angle of a scanned signal means that at any interval of time, a signal from a source operating at a wavelength is impinged upon the sensing optic's interface at an angle of incidence. At a subsequent interval of time, the signal from the same source operating at the wavelength is impinged upon the interface at a different angle of incidence.

Although this disclosure refers to electromagnetic radiation using the terms "signal," "light," "emission," and the like, these references are actually intended to include wavelengths outside the bounds of visible light. Further, while the discussion herein may have focused on a particular wavelength, it will be appreciated that the disclosed sensor 10 can be configured to handle any suitable wavelength of electromagnetic radiation, including wavelengths in the ultraviolet, visible, near infrared, and infrared regions of the electromagnetic spectrum. Finally, the disclosed sensor 10 can use various types of sensing optic shapes, lens systems, scanners, sources, and detectors depending upon the dynamic range requirements of the sensor 10 and the physical dimensions of the sensor 10 dictated by packing requirements.

As disclosed herein, the adaptive optical element or scanner 16, for example, can be a scanning mirror. In general, the adaptive optical element 16 can be a scanning reflective, diffractive, or refractive optic. For example, the adaptive optical element 16 can be a Liquid Crystal on Silicon (LCoS) element or a Micro-Electro Mechanical System (MEMS) micro-mirror, both of which are referred to as Micro-Optical Electro-Mechanical System (MOEMS) elements. For its part, the source 12 can have one or more light emitting diodes (LEDs), laser diodes (LDs), vertical cavity side emitting lasers (VCSELs), super-luminescent light emitting diodes (SLEDs), tungsten halogen lamps, metal halide lamps, deuterium lumps, xenon lamps, line sources, flash lamps, or other broadband sources.

The foregoing description of preferred and other embodiments is not intended to limit or restrict the scope or applicability of the inventive concepts conceived of by the Applicants. Features related to one embodiment disclosed herein can be applied to other embodiments disclosed herein based on the benefit of the present disclosure. In exchange for disclosing the inventive concepts contained herein, the Applicants desire all patent rights afforded by the appended claims. Therefore, it is intended that the appended claims include all modifications and alterations to the full extent that they come within the scope of the following claims or the equivalents thereof.

What is claimed is:

1. A refractive index sensor, comprising:
a source generating an input signal;
an adaptive optical element optically coupled to the source and routing the input signal at sequential angles;
a sensing optic optically coupled to the adaptive optical element and having an interface with a sample;
at least one detector optically coupled to the sensing optic and detecting one or more reflected signals from the interface, the one or more reflected signals indicative of any of the sequential angles of the input signal that are at least equal to or greater than a critical angle of reflection at the interface, the at least one detector optically coupled to the adaptive optical element and detecting at least one direct signal directly from the adaptive optical element; and
a processor operably coupled to the at least one detector, the processor determining a refractive index value from the one or more reflected signals and the direct signal and correlating the refractive index value to a characteristic associated with the sample.

2. The sensor of claim 1, wherein the source comprises one or more light emitting diodes (LEDs), laser diodes (LDs), vertical cavity side emitting lasers (VCSELs), super-luminescent light emitting diodes (SLEDs), tungsten halogen lamps, metal halide lamps, deuterium lumps, xenon lamps, line sources, or flash lamps.

3. The sensor of claim 1, wherein the adaptive optical element comprises a scanning reflective, diffractive, or refractive optic; a Micro-Optical Electro-Mechanical System (MOEMS) element; a Liquid Crystal on Silicon (LCoS) element; or a Micro-Electro Mechanical System (MEMS) micro-mirror.

4. The sensor of claim 1, wherein the sensing optic comprises a material selected from the group consisting of sapphire, ruby, zircon, cubic zirconium, and diamond.

5. The sensor of claim 1, wherein the sensing optic comprises a material having a known index of refraction at least greater than 1.45.

6. The sensor of claim 1, wherein the at least one detector comprises:
   a measurement detector optically coupled to the sensing optic; and
   a reference detector optically coupled to the adaptive optical element.

7. The sensor of claim 1, wherein the at least one detector comprises a measurement detector optically coupled to both the adaptive optical element and the sensing optic and detecting the direct signal from the adaptive optical element and the one or more reflected signals from the sensing optic.

8. The sensor of claim 1, wherein the at least one detector comprises one or more single-element photodiodes, multi-element photodiodes, avalanche photodiodes, photomultiplier tubes, micro-channel plates, bolometers, and thermopiles.

9. The sensor of claim 1, wherein the at least one detector comprises a plurality of sensing elements detecting multiple measurement wavelengths simultaneously.

10. The sensor of claim 1, wherein the processor is operatively coupled to the adaptive optical element and controls the adaptive optical element in routing the input signal at the sequential angles.

11. The sensor of claim 1, wherein the source comprises two or more source elements each generating a different wavelength, and wherein the processor is operatively coupled to the source and selectively configures the wavelength for the input signal using the two or more source elements.

12. The sensor of claim 1, wherein the processor determines the refractive index value of the sample based on the response of the measurement detector and the direct signal indicative of scan rate of the adaptive optical element.

13. The sensor of claim 1, wherein the processor obtains at least one reading indicative of at least one environmental condition of the sample and corrects the determined refractive index value of the sample with the at least one reading.

14. The sensor of claim 13, wherein the at least one reading is indicative of temperature and pressure of the sample.

15. The sensor of claim 1, further comprising a housing having a flow passage for the sample, the sensor housed in the housing, the interface of the sensing optic exposed to the flow passage.

16. The sensor of claim 1, wherein the interface of the sensing optic disposed in a housing is exposed to the fluid to be measured.

17. The sensor of claim 1, further comprising a housing having a sample chamber for the sample, the sensor housed in the housing, the interface of the sensing optic exposed to the sample chamber.

18. The sensor of claim 1, further comprising a fluid analysis device at least including the source, the adaptive optical element, the sensing optic, and the at least one detector.

19. The sensor of claim 18, further comprising a tool housing deployable downhole and having the flow passage for the fluid sample, the fluid analysis device disposed in the tool housing relative to the flow passage.

20. The sensor of claim 1, wherein the processor correlates the refractive index value to the characteristic comprising an indication of: an environmental condition of the sample, a chemical composition of the sample, presence of gas in the sample, presence of emulsified material in the sample, or presence of slug flow in the sample.

21. The sensor of claim 1, wherein the direct signal is indicative of a timing of the sequential angles, and wherein the processor determines the refractive index value from the one or more reflected signals and the timing of the sequential angles.

22. The sensor of claim 1, the direct signal is indicative of a source intensity of the input signal, and wherein the processor compares a measurement intensity of the one or more reflected signals relative to the source intensity.

23. A refractive index analysis method, comprising:
   generating an input signal;
   routing the input signal at sequential angles into a sensing optic;
   interacting the input signal in the sensing optic with an interface between the sensing optic and a sample;
   detecting one or more reflected signals from the interface, the one or more reflected signals indicative of the sequential angles of the input signal that are at least equal to or greater than the critical angle of reflection at the interface;
   detecting a direct signal of the input signal;
   determining with a processor a refractive index value from the one or more reflected signals and the direct signal; and
   correlating with the processor the determined refractive index value to a characteristic associated with the sample.

24. The method of claim 23, wherein generating an input signal comprise operating a source, the source comprising one or more light emitting diodes (LEDs), laser diodes (LDs), vertical cavity side emitting lasers (VCSELs), super-luminescent light emitting diodes (SLEDs), tungsten halogen lamps, metal halide lamps, deuterium lumps, xenon lamps, line sources, or flash lamps.

25. The method of claim 23, wherein routing the input signal comprises operating an adaptive optical element optically coupled to the input signal, the adaptive optical element comprising a scanning reflective, diffractive, or refractive optic; a Micro-Optical Electro-Mechanical System (MOEMS) element; a Liquid Crystal on Silicon (LCoS) element; or a Micro-Electro Mechanical System (MEMS) micro-mirror.

26. The method of claim 23, wherein the sensing optic comprises a material having an index of refraction at least greater than 1.45.

27. The method of claim 23, wherein detecting the direct signal of the input signal comprises directly detecting the input signal, the directly detected input signal indicative of a time signature of the routed input signal.

28. The method of claim 27, further comprising determining operational status of the input signal based on whether the input signal is directly detected.

29. The method of claim 23, wherein detecting one or more reflected signals from the interface comprises detecting the one or more reflected signals at a detector, the detector selected from the group consisting of a single-element photodiode, a multi-element photodiode, an avalanche photodiode, a photomultiplier tube, a micro-channel plate, a bolometer, and a thermopile.

30. The method of claim 23, further comprising selectively configuring a wavelength for the input signal.

31. The method of claim 23, wherein determining the refractive index value of the sample is based on a scan rate of the routed input signal.

32. The method of claim 23, wherein the characteristic comprises an indication of: an environmental condition of the sample, a chemical composition of the sample, presence of gas in the sample, presence of emulsified material in the sample, or presence of slug flow in the sample.

33. The method of claim 23, further comprising:
   obtaining at least one reading of at least one environmental condition of the sample; and correcting the determined refractive index value of the sample with the at least one reading.

34. The method of claim 33, wherein the at least one reading is indicative of a temperature and a pressure of the sample.

35. The method of claim 23, further comprising:

passing the sample through a flow passage, housing the sample in a chamber,
- disposing at least the interface of the sensing optic into the sample, or
- obtaining the sample with a downhole tool deployed downhole; and analyzing the sample with the refractive index analysis method.

* * * * *